United States Patent

Barron et al.

[11] Patent Number: 5,989,272
[45] Date of Patent: Nov. 23, 1999

[54] KERATOME FOR PERFORMING EYE SURGERY AND METHOD FOR USING SAME

[75] Inventors: Mark B. Barron; Milford Barron, both of Grand Blanc, Mich.

[73] Assignee: Barron Precision Instruments L.L.C., Grand Blanc, Mich.

[21] Appl. No.: 09/166,268

[22] Filed: Oct. 5, 1998

[51] Int. Cl.$^6$ .................................................... A61F 9/00
[52] U.S. Cl. .......................................... 606/166; 606/161
[58] Field of Search .................................. 606/166, 161, 606/167, 170, 171, 107; 128/898

[56] References Cited

U.S. PATENT DOCUMENTS

| | | |
|---|---|---|
| Re. 35,421 | 1/1997 | Ruiz et al. . |
| 4,750,491 | 6/1988 | Kaufman et al. ........................ 606/166 |
| 4,840,175 | 6/1989 | Peyman . |
| 4,903,695 | 2/1990 | Warner et al. . |
| 5,288,292 | 2/1994 | Giraud . |
| 5,314,439 | 5/1994 | Sugita ..................................... 606/166 |
| 5,342,378 | 8/1994 | Giraud et al. . |
| 5,556,406 | 9/1996 | Gordon et al. . |
| 5,586,980 | 12/1996 | Kremer et al. . |
| 5,595,570 | 1/1997 | Smith . |
| 5,624,456 | 4/1997 | Hellenkamp . |
| 5,632,757 | 5/1997 | Arnott ..................................... 606/166 |

*Primary Examiner*—Michael Buiz
*Assistant Examiner*—Kevin Truong
*Attorney, Agent, or Firm*—Brooks & Kushman P.C.

[57] ABSTRACT

A keratome (10) and a method for using the keratome (10) for cutting a cornea of an eye (14) are provided which allow an operator to view the cutting operation as it occurs. The keratome (10) includes an annular housing (12) sized to contact the eye (14) and allow a portion (21) of the cornea to protrude therein. A motor housing (22) is mounted to the annular housing (12) for movement with respect thereto in a feed direction. A blade (36) is mounted by the motor housing (22) for movement in a cutting direction transverse to the feed direction, and a motor (26) mounted by the motor housing (22) is drivingly connected to the blade (36) to provide reciprocal movement thereof in the cutting direction. Movement of the motor housing (22) in the feed direction across the eye (14) accompanied by movement of the blade (36) in the cutting direction cuts the portion (21) of the cornea protruding into the annular housing (12), while an operator can view the cutting through the annular housing (12).

27 Claims, 4 Drawing Sheets

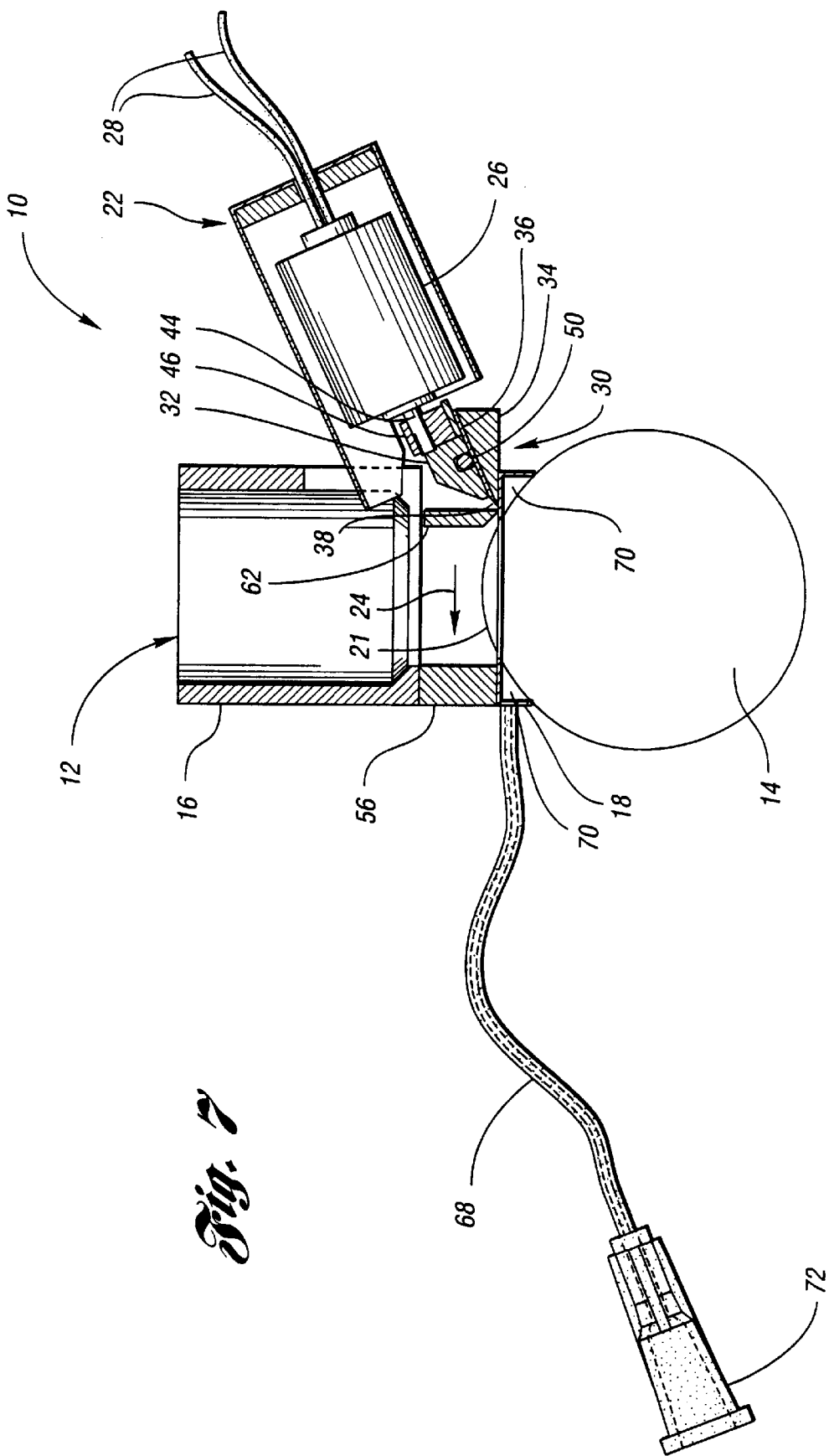

KERATOME FOR PERFORMING EYE SURGERY AND METHOD FOR USING SAME

TECHNICAL FIELD

This invention relates to surgical devices, and more particularly to a keratome and a method for using the keratome to perform resections of the eye.

BACKGROUND ART

Refractive surgery is a method of treating myopia, hyperopia, astigmatism, and other corneal abnormalities in human beings. This process involves reshaping a portion of the cornea, the transparent outer layer of the eye, to change its effective curvature. In recent refractive surgical methods, a preselected layer from the anterior surface of the cornea is removed in order to modify the tissue underneath. The corneal layer may be removed completely, as described in U.S. Pat. No. 4,840,175 issued to Peyman, but preferably the layer remains connected to the cornea as a hinged flap.

Included in refractive surgical methods is lamellar keratectomy, as described in U.S. Pat. No. 5,556,406 issued to Gordon et al., wherein a first layer of the cornea is raised, a second layer of the cornea may be removed, and then the first layer is replaced. Alternatively, laser intrastromal keratomileusis, or LASIK, procedures utilize a laser to reprofile the surface underlying the raised corneal layer in order to modify the corneal curvature, as described in U.S. Pat. No. 4,903,695 issued to Warner et al.

Different devices have been designed for performing refractive surgery on patients. One such device is a keratome, which has a motorized cutting blade for performing resections of the cornea. The blade in a keratome oscillates from side to side at high speed to cut the corneal tissue, while the blade is manually pushed or automatically driven in a path across the eye.

Keratomes typically include a suction ring, which is placed on the eye to position the cornea for cutting. In addition, a horizontal plate is assembled onto the suction ring. When placed over the eye, the suction ring draws the cornea therethrough to flatten it against the horizontal plate for slicing by the blade. Examples of such keratomes can be found in U.S. Pat. No. 5,586,980 issued to Kremer et al., U.S. Pat. No. 5,342,378 issued to Giraud et al., U.S. Pat. No. 5,595,570 issued to Smith, U.S. Pat. No. 5,624,456 issued to Hellenkamp, and U.S. Pat. No. RE 35,421 issued to Ruiz et al. The vertical spacing between the plate and the blade determines the depth or thickness of the cut. The setting of the blade is extremely critical, and the depth of the cut must be known precisely and accurately. For example, U.S. Pat. No. 5,288,292 issued to Giraud et al. discloses a keratome having a differential micrometer to adjust the depth of cut.

Due to their use of a horizontal plate structure, prior art keratomes have two main disadvantages. First, the horizontal plate obstructs an operator's view of the eye, preventing the operator from monitoring the corneal resection. As a consequence, an operator is not able to make informed decisions regarding altering or aborting the cut during the procedure. Second, keratomes are usually dependent on the use of a vacuum for proper functioning, in order to bring the cornea flat against the horizontal plate to position the cornea for cutting by the blade. However, a suction source is not always available, or may malfunction during the procedure. Furthermore, patients with high myopia have a tendency for retinal detachment, a condition which may be aggravated by the use of suction in this manner.

Disclosure of the Invention

Therefore, it is an object of the present invention to provide a keratome and a method for using the keratome which allows an operator to view the cutting of the cornea as it occurs.

It is a further object of the present invention to provide a keratome and a method for using the keratome that does not require the use of a suction source for corneal resection.

It is another object of the present invention to provide a keratome and a method for using the keratome that produces a more accurate cut of the cornea.

It is yet another object of the present invention to provide a keratome that is inexpensive to produce and maintain.

Accordingly, a keratome and a method for using the keratome for cutting a cornea of an eye are provided which allow an operator to view the cutting operation as it occurs. The keratome includes an annular housing sized to contact the eye and allow the cornea to protrude therein. A motor housing is mounted to the annular housing for movement with respect to thereto in a feed direction. A blade is mounted by the motor housing for movement in a cutting direction transverse to the feed direction, and a motor mounted by the motor housing is drivingly connected to the blade to provide reciprocal movement thereof in the cutting direction. Movement of the motor housing in the feed direction across the eye accompanied by movement of the blade in the cutting direction cuts a portion of the cornea protruding into the annular housing, while an operator can view the cutting through the annular housing.

The above objects and other objects, features, and advantages of the present invention are more readily understood from a review of the attached drawings and the accompanying specification and claims.

BRIEF DESCRIPTION OF THE DRAWINGS

FIG. 7 is a side, sectional view of an alternative embodiment of the keratome of the present invention wherein a suction source is utilized.

BEST MODES FOR CARRYING OUT THE INVENTION

Figure 1:
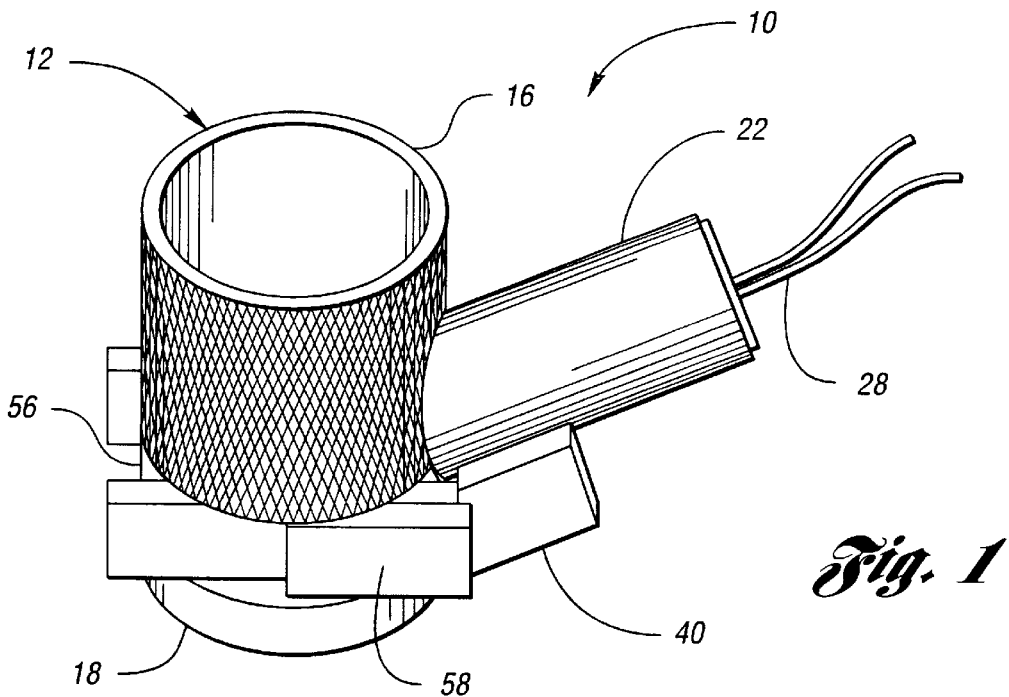
FIG. 1 is a perspective view of a keratome constructed in accordance with the present invention.
Figure 2:
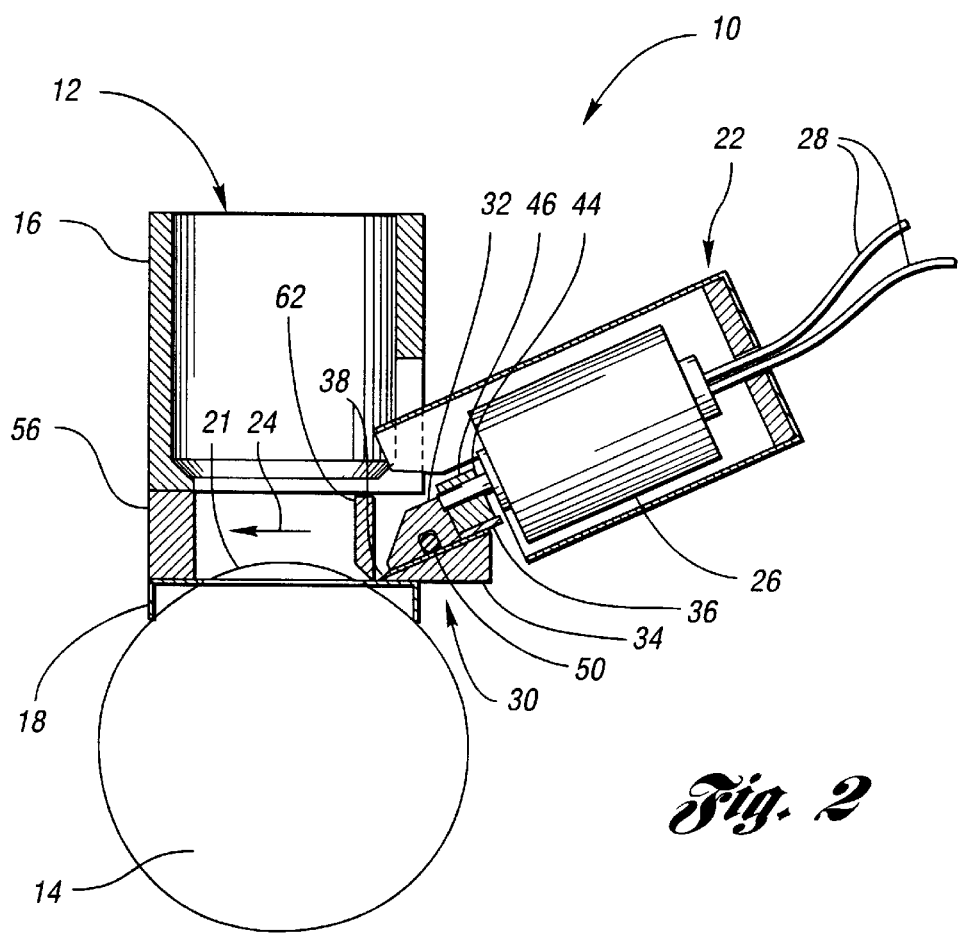
FIG. 2 is a side, sectional view of the keratome as it engages a patient's eye.
Figure 3:
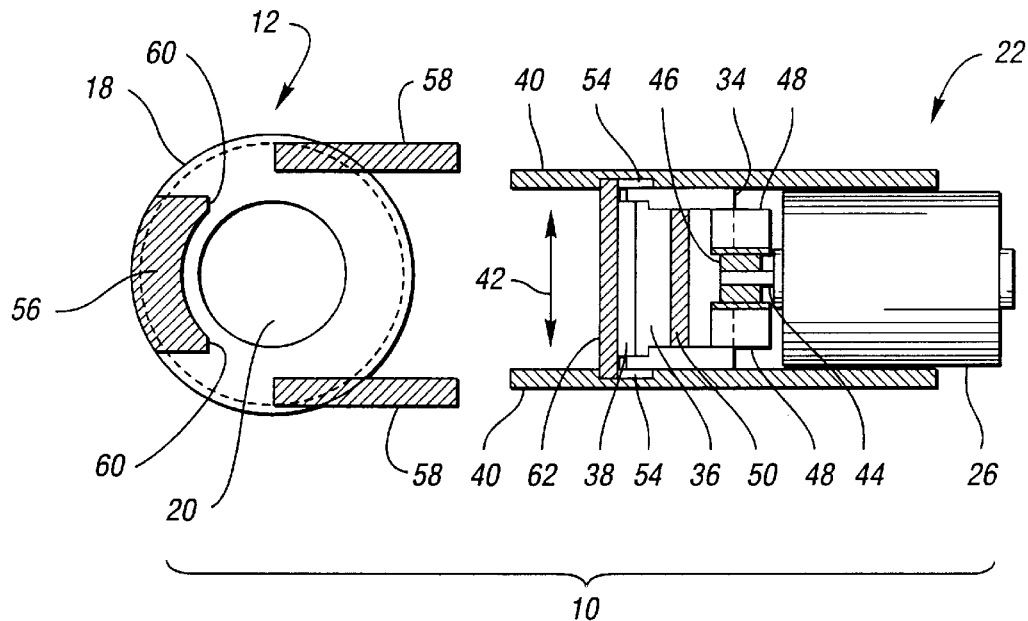
FIG. 3 is a top, sectional view of an annular housing separated from a motor housing of the keratome.

A keratome constructed according to the present invention and used to perform the method of the present invention is generally indicated by reference numeral 10 in FIGS. 1–3. Keratome 10 is used to perform resections of the cornea of the eye while allowing an operator to simultaneously view the procedure. More specifically, keratome 10 is designed to cut substantially, but not necessarily completely, across the cornea so as to raise a layer thereof and create a hinged flap of corneal tissue. Once the flap is created, modifications can be made to the flap itself or to the corneal tissue lying underneath. The desired result of this procedure is that, after positioning the flap back on the cornea, the cornea will have a new curvature, and therefore a new refracting surface for improved vision.

As keratome 10 is described herein, any reference to direction is for exemplary purposes only. The keratome of the present invention can be held and used for cutting in any direction or orientation, and can be used for corneal resections of either a patient's right or left eye.

Referring to FIGS. 1–3, keratome 10 includes an annular housing 12 which is placed over a patient's eye 14 while allowing an operator to clearly view the eye 14 through annular housing 12. Annular housing 12 is preferably made of stainless steel, and includes an upper holding cylinder 16 that is preferably knurled for easy gripping by an operator. Below holding cylinder 16, annular housing 12 is provided with a positioning ring 18 for engaging and positioning the eye 14 for corneal resection. Preferably, positioning ring 18 is circular in shape and has a concentric aperture 20 formed therein. Aperture 20 is sized sufficiently to permit a portion 21 of the anterior surface of the cornea to protrude therethrough naturally, without having to force the eye upward. As a result, keratome 10 of the present invention is capable of engaging and positioning eye 14 for cutting without the use of a suction source, as will be described in greater detail below.

Still referring to FIGS. 1–3, a motor housing 22 is mounted to annular housing 12 for movement with respect thereto in a feed direction designated generally by arrow 24. Specifically, motor housing 22 is mounted between holding cylinder 16 and positioning ring 18 such that motor housing 22 is free to move in the feed direction 24 but is constrained from moving vertically. Motor housing 22, like annular housing 12, is preferably formed from stainless steel. Mounted within motor housing 22 is a motor 26, which is preferably electrically operated and capable of operating at a constant speed, regardless of load. Motor 26 is connected to a power source (not shown) via wires 28, and in a preferred embodiment is controlled by a foot pedal or similar mechanism.

Motor housing 22 is further provided with a blade subassembly 30 mounted therein. Blade subassembly 30 includes a top blade support 32 and a bottom blade support 34 which hold a blade 36 therebetween, such that a sharpened cutting edge 38 of blade 36 is exposed. To produce the desired cut of the cornea, blade 36 is preferably disposed within blade subassembly 30 at about 25° from the horizontal plane defined by positioning ring 18. In addition, cutting edge 38 is preferably formed to have an angle of approximately 15° from the horizontal axis of blade 36. Top blade support 32 and bottom blade support 34 are affixed between two side frames 40 provided on motor housing 22, as shown in FIG. 3.

Typically, keratomes are intended to be reusable, such that the keratome must be sterilized between uses. This procedure is time consuming, and autoclaving the keratome can damage the motor and other moving parts. In addition, the blades have limited life spans and require regular replacement to ensure accurate cutting. In contrast, keratome 10 of the present invention is preferably disposable and intended for a single use. Annular housing 12, motor housing 22, and the components thereof may be constructed inexpensively such that the cost per unit is not prohibitive and is outweighed by the precision gained by using a new unit for each procedure.

In addition, keratome 10 of the present invention is constructed using low-temperature processes as opposed to high temperature welding or soldering typically used for such devices. First, the components of keratome 10 are formed separately by a process such as injection molding, rather than by machining the parts which could cause them to warp. The component parts are then assembled at room temperature using a liquid bonding material, such as a urethane methacrylate ester or an ethyl cyanoacrylate. The low-temperature bonding process utilized allows for precise alignment of component parts without the warping associated with welding or soldering, thereby ensuring the proper functioning of keratome 10.

Figure 4:
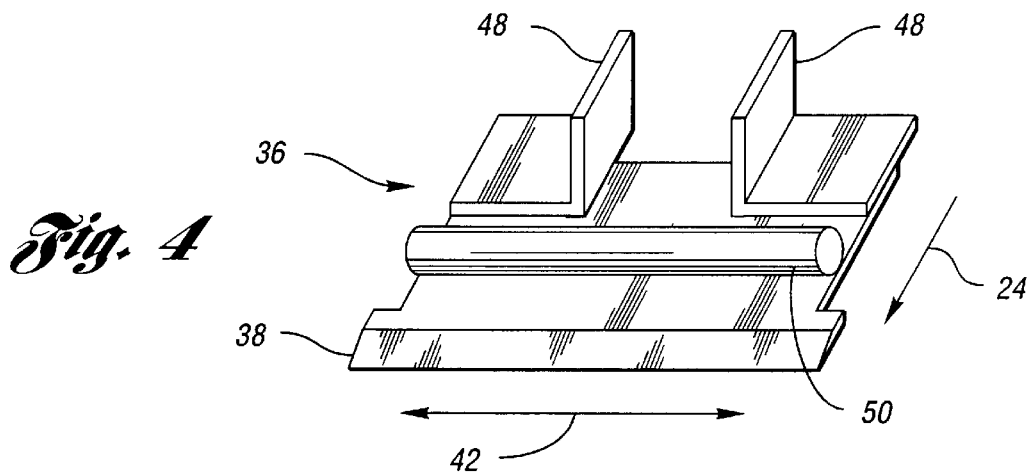
FIG. 4 is an enlarged view of a blade of the keratome.

In order cut the cornea, blade 36 is reciprocated in a cutting direction 42 by motor 26 which is generally transverse to feed direction 24, as shown in FIG. 3. Motor 26 is provided with a drive shaft 44 extending therefrom to which an eccentric cam 46 is mounted. Affixed to blade 36 are cam followers 48, which may resemble angle brackets as shown in FIGS. 3 and 4, or alternatively may be formed as a single U-shaped part. Blade 36 is positioned between top blade support 32 and bottom blade support 34 so that cam followers 48 abut either side of eccentric cam 44. With this configuration, the rotation of drive shaft 44 and attached eccentric cam 46 acts to impart an oscillatory motion to blade 36 in the cutting direction 42 via cam followers 48. In addition to cam followers 48, blade 36 also has a locating pin 50 (FIGS. 2–4). Top blade support 32 has a slot 52 sized to receive locating pin 50 which is formed along the cutting direction 42, such that the movement of blade 36 is controlled. Alternatively, locating pin 50 could be affixed to the opposite side of blade 36, and slot 52 be provided in bottom blade support 34.

Figure 5:
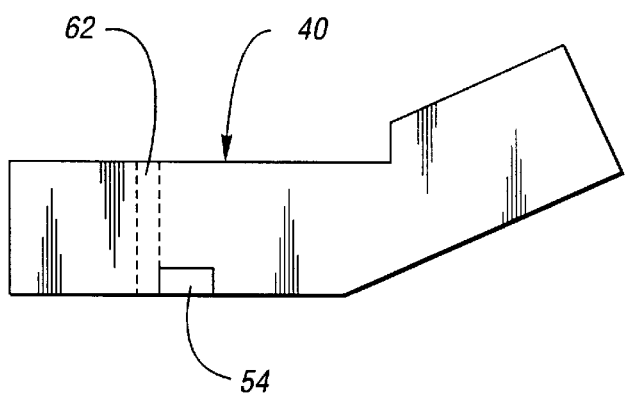
FIG. 5 is an enlarged view of a side frame of the motor housing of the keratome.

Since the cornea is viscous in nature, the speed and amplitude of the cutting motion must be sufficient to prevent deforming or bunching of the cornea. In the present invention, blade 36 is of a light mass such that a high oscillation speed of approximately 20,000 rpm may be employed. To increase the available amplitude of the cutting motion, side frames 40 preferably each have a notch 54 formed therein, as shown in FIGS. 3 and 5, allowing blade 36 to travel further during its side to side movement.

Figure 6A:
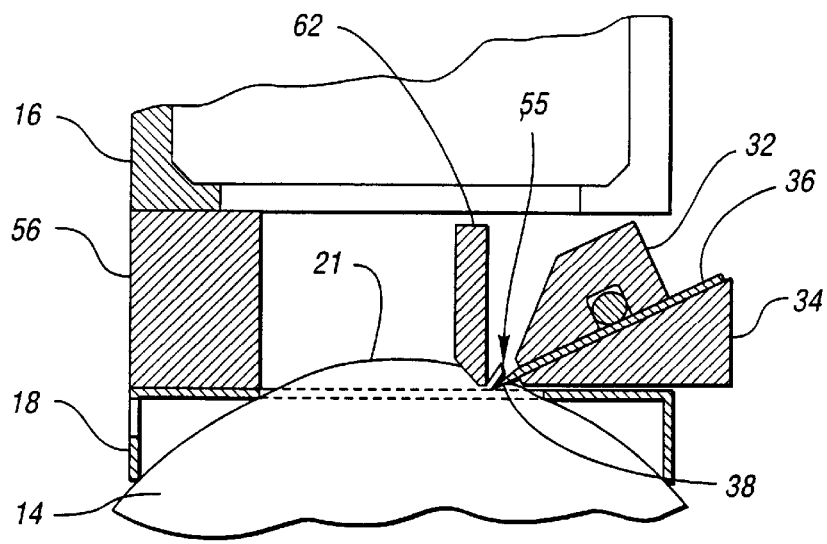
FIGS. 6a, 6b, and 6c are sectional views of the control bar and blade assembly of the keratome as they contact the cornea portion of the eye before, during, and after creation of the corneal flap, respectively.
Figure 6B:
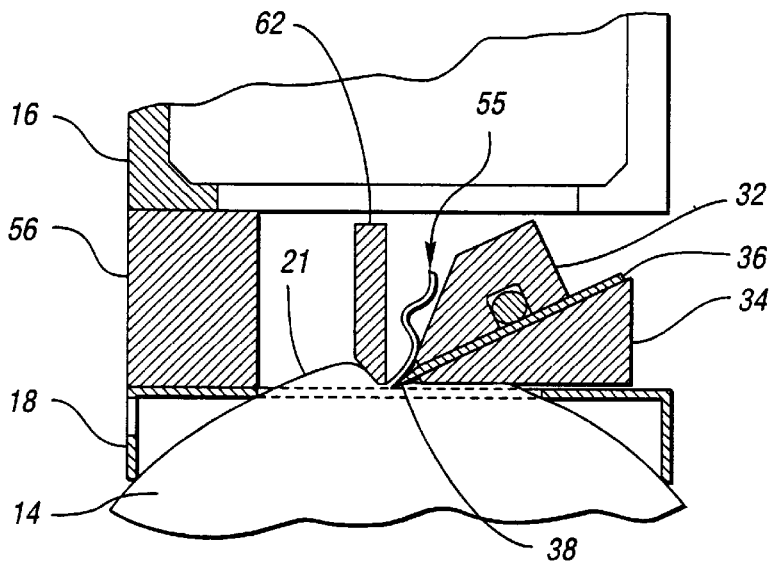
Figure 6C:
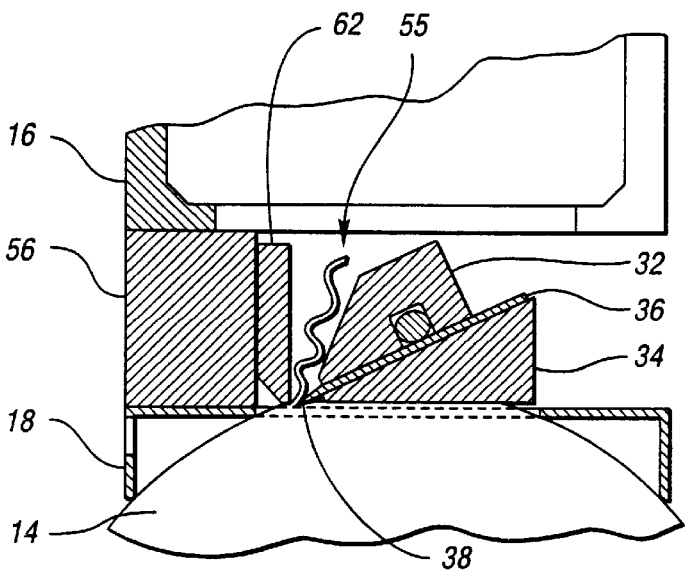

FIGS. 6a, 6b, and 6c depict the use of keratome 10 before, during and after resecting a flap 55 from the cornea portion 21 of the eye 14, respectively. In the views of FIGS. 6a–6c, annular housing 12 is included in part, and motor housing 22 has been removed for clarity. In operation, motor 26 oscillates blade 36 in the cutting direction 42 while motor housing 22 is moved in the feed direction 24 and annular housing 12 is held stationary in position on a patient's eye 14. Positioning ring 18 provides a fixed support along which side frames 40 slide in order for blade 36 to resect the corneal flap. Preferably, motor housing 22 is moved manually in the feed direction 24 by an operator to allow for greater control of the procedure. In particular, upon viewing the resection through annular housing 12, an operator may determine that the cut needs to be altered or aborted entirely. Alternatively, a motor or other such device could be used to automate the movement of motor housing 22 in the feed direction 24.

To control the movement of motor housing 22 with respect to annular housing 12, annular housing 12 preferably includes a front stop 56 (FIGS. 3 and 6) and side guides 58 (FIG. 3) formed between holding cylinder 16 and positioning ring 18. Front stop 56 is preferably semicircular in shape and is provided with edges 60 adjacent aperture 20. which serve to limit the travel of motor housing 22 with respect to annular housing 12, and therefore limit the length of the corneal flap 55 resected. Side guides 58 comprise substantially planar walls extending along the sides of positioning ring 18 which function to direct the movement of motor housing 22 across the eye during the surgical cutting of the cornea. Side frames 40 of motor housing 22 slide between side guides 58 of positioning ring 18.

Referring to FIGS. 2, 3, and 6, motor housing 22 further includes a control bar 62 for determining the depth at which the cornea portion 21 is resected by blade 36. Control bar 62 is positioned to precede blade 36 across the eye 14, and is preferably tapered to allow for smooth movement across the eye 14. Unlike the horizontal plates utilized in prior art keratomes, control bar 62 of the present invention is mounted vertically within motor housing 22, extending in a plane substantially perpendicular to a transverse plane of annular housing 12. With this configuration, an operator is able to view the eye 14 as the corneal flap 55 is being cut. Without requiring the use of a suction source, control bar 62 engages cornea portion 21 protruding through aperture 20 of positioning ring 18 to control the depth of cut by blade 36, as best shown in FIG. 6b.

The mounted placement of control bar 62 within motor housing 22 is selected to correspond to the desired dimensions of the cut to be made into the cornea. In a preferred embodiment, control bar 62 is mounted about 0.006 inches above and about 0.003 inches preceding the cutting edge 38 of blade 36. This placement of control bar 62 corresponds with the creation of a corneal flap 55 which includes the epithelial layer, Bowman's membrane, and a segment of the corneal stroma. As described previously, the length of the corneal flap 55 is limited by front stop 56, which control bar 62 will abut as motor housing 22 is moved across the eye 14, as shown in FIG. 6c. Keratome 10 of the present invention may be constructed using control bars 62 of different vertical or horizontal dimensions or mounting locations to offer variations in the depth and length of corneal flap 55.

Since the corneal flap 55 is typically replaced on the eye without suturing, it is important to create a cut which allows the flap to locate as well as possible in its original location. In the present invention, control bar 62 is closer to the top of positioning ring 18 than are horizontal plates used in prior art devices. The positioning of control bar 62 has the effect of creating a cut with steeper corners compared with the profile created by previous methods, allowing the corneal flap 55 to better locate in its original position.

In an alternative embodiment of the present invention depicted in FIG. 7, positioning ring 18 may be temporarily attached to the eye 14 using a suction source. As indicated above, suction is not necessary to bring cornea portion 21 into contact with control bar 62 as in prior art devices, but may be utilized to increase the uniformity of the cut even further. In this embodiment, a connection tube 68, such as a silicone tube, is provided in fluid communication with an undersurface 70 of positioning ring 18. Connection tube 68 may be connected to a suction source, such as a vacuum (not shown), such that when suction occurs the undersurface 70 of positioning ring 18 forms a seal and is retained in position on the eye 14.

Prior art keratomes typically have elongated housing structures, such that the motor is located some distance from the positioning ring. As a result, vacuum pressures on the order of 65–100 mm Hg are required to hold the positioning ring in place due to the torque created by the weight of the motor. In keratome 10 of the present invention, motor 26 is located in close vertical proximity to positioning ring 18, such that vacuum pressures as low as 20 mm Hg may be utilized.

Given this minimal pressure requirement, a powered vacuum source may be utilized, or alternatively a suction source as simple as a syringe is sufficient. Use of a syringe (not shown) obviates the need for sophisticated control electronics, and allows a filter 72 (FIG. 7) to be attached directly to connection tube 68 for removing particulate matter. For instance, a hydrophobic 0.45 $\mu$m filter could be used for this purpose. The simplicity with which a suction source such as this could be utilized with keratome 10 of the present invention provides an increased versatility of keratome 10 compared with prior art devices.

In summary, the present invention provides a keratome and a method for using the keratome which allows an operator to perform an accurate corneal resection while simultaneously viewing the procedure. This is accomplished through the use of an annular housing which is used to contact the eye, and a vertically oriented control bar which precedes the blade across the eye, but does not obstruct the vision of the operator. A suction source is not required for proper functioning of the keratome, as the cornea protrudes into the annular housing to a sufficient extent in the absence of vacuum pressure to be engaged by the control bar and subsequently the blade. The keratome provides blade operation which is characterized by a high speed and amplitude of oscillation, and produces a cut which results in improved locating capabilities for the corneal flap. If desired, the keratome of the present invention may be connected to a suction source to provide increased uniformity of the resection procedure.

It is understood, of course, that while the form of the invention herein shown and described constitutes a preferred embodiment of the invention, it is not intended to illustrate all possible forms thereof. It will also be understood that the words used are words of description rather than limitation, and that various changes may be made without departing from the spirit and scope of the invention disclosed.

What is claimed is:

1. A keratome for cutting a cornea of an eye, the keratome comprising:
   an annular housing sized to contact the eye and allow the cornea to protrude therein;
   a motor housing mounted on the annular housing for movement with respect thereto in a feed direction;
   a blade mounted by the motor housing for movement in a cutting direction transverse to the feed direction;
   a motor mounted by the motor housing and drivingly connected to the blade to provide reciprocal movement thereof in the cutting direction, such that movement of the motor housing in the feed direction across the eye accompanied by movement of the blade in the cutting direction cuts a portion of the cornea protruding into the annular housing, while an operator can view the cutting through the annular housing.

2. The keratome of claim 1, further comprising a control bar mounted by the motor housing which precedes the blade across the eye to determine the depth of cut of the cornea.

3. The keratome of claim 2, wherein the control bar is mounted to extend in a plane substantially perpendicular to a transverse plane of the annular housing so as not to obscure the operator's view through the annular housing.

4. The keratome of claim 1, wherein the annular housing includes a positioning ring having an aperture through which the cornea protrudes.

5. The keratome of claim 1, wherein the annular housing includes a holding cylinder for the operator to grip.

6. The keratome of claim 1, wherein the motor includes a drive shaft extending therefrom and an eccentric cam mounted to the drive shaft.

7. The keratome of claim 6, wherein the blade includes cam followers between which the eccentric cam is received to provide the reciprocal driving of the blade.

8. The keratome of claim 1, further comprising a top blade support and a bottom blade support mounted by the motor housing, wherein the blade is held between the top blade support and the bottom blade support.

9. The keratome of claim 8, wherein the blade includes a locating pin, and either the top blade support or the bottom blade support includes a slot sized to receive the locating pin to control the movement of the blade.

10. The keratome of claim 1, wherein the motor housing includes side frames.

11. The keratome of claim 10, wherein the side frames each have a notch to allow increased travel of the blade in the cutting direction.

12. The keratome of claim 1, wherein the annular housing includes side guides which guide the movement of the motor housing across the eye.

13. The keratome of claim 1, wherein the annular housing includes a front stop to limit the movement of the motor housing across the eye.

14. The keratome of claim 1, wherein the blade is mounted in the motor housing at an angle of about 25°.

15. The keratome of claim 1, wherein the blade includes a cutting edge which is angled at about 15° from the horizontal axis of the blade.

16. The keratome of claim 1, further comprising a suction source operably connected to the annular housing for temporarily securing the eye to the annular housing.

17. The keratome of claim 16, wherein the suction source is a powered vacuum source.

18. The keratome of claim 16, wherein the suction source is a syringe.

19. The keratome of claim 1, further comprising a filter operably connected to the annular housing.

20. The keratome of claim 1, wherein the keratome is disposable.

21. The keratome of claim 1, the keratome is constructed from stainless steel.

22. The keratome of claim 1, wherein the keratome is formed by a low-temperature bonding process.

23. The keratome of claim 1, wherein the motor housing is moved manually across the eye.

24. A method for cutting a cornea of an eye, the method comprising:

viewing the cornea through an annular housing placed on the eye with the cornea protruding into the annular housing; and moving a motor housing movably mounted on the annular housing in a feed direction across the eye while moving a blade mounted by the motor housing in a cutting direction transverse to the feed direction in order to cut a portion of the cornea while viewing the operation.

25. The method of claim 24, further comprising controlling the depth of cut using a control bar mounted in the motor housing which precedes the blade across the eye without obstructing the view of an operator.

26. The method of claim 24, wherein moving the motor housing across the eye is accomplished manually by an operator.

27. The method of claim 24, further comprising temporarily securing the eye to the annular housing using a suction source.

* * * * *